US009204709B2

(12) United States Patent
Paulsen et al.

(10) Patent No.: US 9,204,709 B2
(45) Date of Patent: Dec. 8, 2015

(54) ORAL HYDRATING MIST APPARATUS

(76) Inventors: Kevin Paulsen, Hogansville, GA (US);
Debra J. Paulsen, Hogansville, GA (US)

( * ) Notice: Subject to any disclaimer, the term of this patent is extended or adjusted under 35 U.S.C. 154(b) by 515 days.

(21) Appl. No.: 13/557,825

(22) Filed: Jul. 25, 2012

(65) Prior Publication Data
US 2013/0026248 A1    Jan. 31, 2013

Related U.S. Application Data

(60) Provisional application No. 61/513,120, filed on Jul. 29, 2011.

(51) Int. Cl.
| | |
|---|---|
| B05B 11/00 | (2006.01) |
| A45F 3/16 | (2006.01) |
| A45F 3/18 | (2006.01) |
| A61M 16/16 | (2006.01) |
| A45F 5/00 | (2006.01) |

(52) U.S. Cl.
CPC ... *A45F 3/16* (2013.01); *A45F 5/00* (2013.01); *A61M 16/16* (2013.01); *A45D 2200/057* (2013.01); *A45F 2003/166* (2013.01); *A45F 2005/008* (2013.01); *A45F 2200/0583* (2013.01); *A61M 2209/088* (2013.01); *A61M 2210/0618* (2013.01); *A61M 2210/0625* (2013.01); *B05B 11/0091* (2013.01); *B05B 11/0094* (2013.01)

(58) Field of Classification Search
CPC ............ B05B 11/0005; B05B 11/0037; B05B 11/0089; B05B 11/0091; B05B 11/0094; A45F 3/16; A45F 5/00; A45F 2003/166; A45F 2005/008; A45F 2200/0583; A61M 16/16; A61M 2209/088; A61M 2210/0618; A61M 2210/0625; A45D 2200/057
USPC ............ 239/24, 33, 152–154, 289, 302, 337, 239/529; 222/175; 224/148.2, 148.4, 148.6; 604/77
See application file for complete search history.

(56) References Cited

U.S. PATENT DOCUMENTS

| | | | | |
|---|---|---|---|---|
| 5,890,636 | A * | 4/1999 | Kibbe | 224/148.6 |
| 8,167,177 | B1 * | 5/2012 | Galgano | 222/175 |
| 2011/0192785 | A1 * | 8/2011 | Pritchard et al. | 210/419 |

* cited by examiner

*Primary Examiner* — Darren W Gorman
(74) *Attorney, Agent, or Firm* — Gardner Groff Greenwald & Villanueva, PC

(57) ABSTRACT

A hydrating system including a pressurized reservoir configured to hold a volume of liquid; and a hydration delivery attachment that is operably coupled to the pressurized reservoir. The hydrating system also may include a base for supporting the pressurized reservoir. The base is configured to releasably secure to an appendage.

18 Claims, 3 Drawing Sheets

ORAL HYDRATING MIST APPARATUS

CROSS-REFERENCE TO RELATED APPLICATION

This application claims the priority benefit of U.S. Provisional Patent Application Ser. No. 61/513,120, filed Jul. 29, 2011, which is hereby incorporated herein by reference.

TECHNICAL FIELD

The present invention relates generally to a hydrating mist apparatus and, in particular, to a portable oral assistance system to supplement inhibited salivary supply apparatus

BACKGROUND

The number of new head and neck cancer incidences around the world is approximately 600,000+/− per year, with approximately 40,000+/− being within the US. Decreased or absent output from the salivary glands and the cells of membranous linings found within the mouth, throat and airway passages has been strongly linked, but is not limited to association with cancer treatments such as radiation and/or some chemotherapy agents, especially those treatments involving head and neck cancers. There is also a significant population of survivors who suffer cancer treatment/radiation induced xerostomia of a permanent nature. Xerostomia (dry mouth) is one of the most widely cited manifestations associated with cancer treatments of the head and neck resulting in decreased salivary gland output.

Saliva production typically begins to decrease very soon after the start of head and/or neck radiation therapy, often within the very first week. This reduction in salivary function continues declining as the treatment progresses. The extent of damage that occurs to the moisture producing capabilities of the salivary glands and functioning of the cells of the membranous linings that lubricate the throat and airways will vary, dependent upon the exact location of the area treated as well as the total dose of radiation that was delivered.

Dry mouth can also be caused by activity, exertion and certain medications or diseases such as Sjrojen's. While this type of dry mouth can be temporary, radiation-therapy-induced xerostomia can in some cases completely destroy salivary gland function, has no known cure at this time and is considered permanent after a certain point in recovery. This means that patients who received treatment for head, neck or chest related cancers likely have an affected ability to produce moisture within the oral cavity and will likely suffer with this condition for the remainder of their lives.

There are a wide variety of bio-engineered, herbal-based and synthetic products and solutions currently available for relief of symptoms of xerostomia. Some of these products may operate through simulation of salivary excretions and some through stimulation of remaining working salivary glands. These products include gums, mouthwashes, sprays, and toothpastes, etc. . . . . While these solutions may offer some relief there are still problems. For example many of these are effective for only short periods, may have limitations upon number of times recommended to be used per day, must be carried and/or applied, may have taste, textures, an oily or otherwise unnatural feel in the mouth. Additionally, the increase or introduction of actual environmental moisture delivered is generally minimal. And, the delivery of the solutions can fail to reach all aspects of oral cavity and may not provide sufficient hydrating lubrication in the form of moisture that is delivered to the membranous linings of airways.

Additionally, severe xerostomia can result in water overload causing feelings of stomach fullness and/or may even be the cause of hyponatremia. It would therefore be desirable to have an oral hydrating system that is convenient, and may be used as often as user wishes, as many times per day without limit as needed.

SUMMARY

In example embodiments, the present embodiment provides a system for hydration through a pressurized reservoir of liquid and a hydration delivery attachment. The hydration delivery attachment allows a user to hydrate a variety of orifices, for example the oral cavity and the respiratory airways. The system can be secured to a user's appendage, for example an arm.

In one aspect, the present invention relates to a hydrating system that includes a pressurized reservoir configured to hold a volume of liquid. The hydrating system also includes a hydration delivery attachment that is operably coupled to the pressurized reservoir.

In another aspect, the present invention relates to a hydrating system that includes a pressurized reservoir configured to hold a volume of liquid. The hydrating system also includes a base for supporting the pressurized reservoir. The base is configured to releasably secure to an appendage.

In still another aspect, the present invention relates to a method for delivering mist hydration. The method includes securing a pressurized reservoir to an appendage. The pressurized reservoir is configured to hold a volume of liquid and includes a valve configured to convert the liquid into mist. The method also includes applying a force to the valve to stimulate the release of liquid from within the reservoir. The liquid is released as mist.

The specific techniques and structures employed to improve over the drawbacks of the prior devices and accomplish the advantages described herein will become apparent from the following detailed description of example embodiments and the appended drawings and claims.

DETAILED DESCRIPTION OF EXAMPLE EMBODIMENTS

The present invention is an oral hydrating mist system intended to deliver moisture to a user's oral cavity in a breathable mist form. The oral hydrating mist system can be worn or carried for convenience. The system includes a pressurized liquid reservoir that has a hydration delivery attachment to deliver liquid contents from the reservoir in a hydrating mist form. The hydration delivery attachment can be used to deliver hydration into an oral cavity and/or airways. The hydrating/moisture mist delivered typically includes airborne droplets of liquid water.

Figure 1:
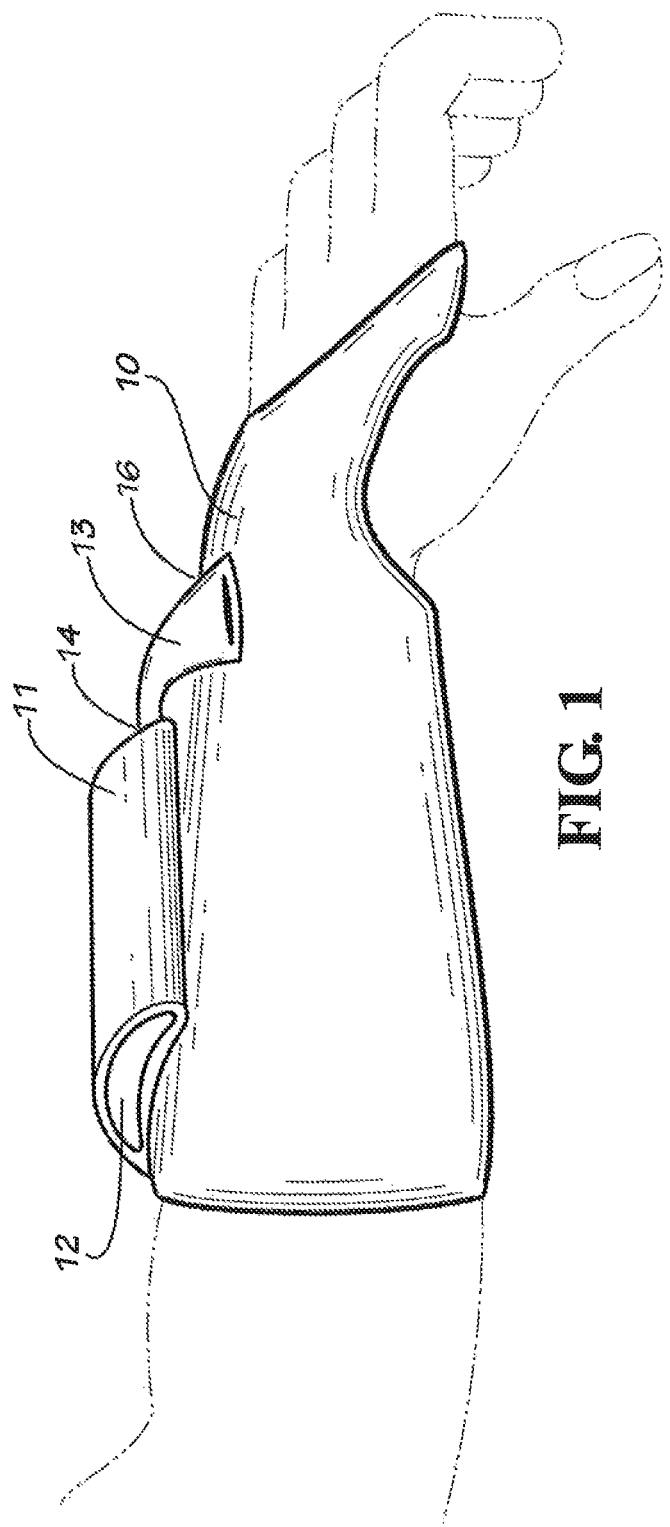
FIG. 1 is a perspective in-use view of a wearable oral hydration apparatus with one example of a housing base having a thumb receiver to improve stability according to a first example embodiment.

With reference to FIG. 1, the oral hydrating mist system includes a wearable base housing 10 that is shown to secure to an appendage, for example an arm. The base housing 10 can be constructed of many different materials such as one of an elastic and/or flexible nature for comfortable fit, very similar to standard design of traditional arm/wrist support braces. As shown, the base housing 10 can have a tube shape with open ends for inserting an appendage. Alternatively, the base housing 10 can be secured to an appendage with any suitable fastener system, for example opposing hook-and-loop fasteners, snaps, straps or other suitable fastener device which allows for an adjustable, comfortable fit. The FIG. 1 example embodiment shows the base housing 10 with additional openings for thumb support to increase stability. Alternatively still, the hydrating system can be carried like a beverage container.

The oral hydrating mist system can also include a reservoir receiver 11 secured to the base housing 10 surface. The reservoir receiver 11 receives and secures a reservoir 12 with respect to the base housing 10. As shown in FIG. 1, the receiver 11 can be a pocket secured to the base housing 10. The pocket 11 shown can be constructed of elastic and flexible material similar to the material used for the housing 10. The additional material used to construct the receiver 11 can be secured to the housing 10 surface through any securing means, for example stitching, hook-and-loop, snaps, glue, or similar means. The receiver 11 can alternatively be constructed of a rigid and durable material to maintain its shape and can be secured to the base 10 in a similar manner as described above. The reservoir receiver can alternatively be a docking station (not shown) that secures a reservoir through corresponding attaching means located on the receiver and the docking station, for example snap, hook-and-loop, slide-and-lock, or similar means.

The reservoir 12 is a container that holds a volume of liquid. As shown, the reservoir 12 container can have a shape similar to a flask, but any size or shape that holds liquid and is comfortable to the user is considered effective. Also, the reservoir 12 container can be constructed of any material that can hold a liquid without leaks, for example plastic or metal, both rigid and flexible. The liquid contents within the reservoir 12 are under pressure, and a pressurize-release spray-dispensing mechanism (also referred to as a pressurization mechanism) is secured to the reservoir to release the pressurized liquid from the reservoir in a spray mist. The pressurization mechanism can be one that is commercially available, such as the pressurization technology used in common aerosol cans. For example, the pressurization mechanism can have a hollow dip tube extending from within the reservoir 12 to a valve stem that exits the reservoir through a valve cup that maintains an airtight and leak-proof seal on the reservoir. As with commercially available aerosol technology, when the valve stem is relaxed, no liquid will exit the reservoir through the tube and stem (i.e., the valve stem is in a closed/containment position). If a downward force is applied to the valve stem, a volume of the pressurized liquid is forced outward through the tube and stem in mist form by a pressurized propellant in the pressurized reservoir (i.e., the valve stem is in an open/release position). Once the downward force is removed, the internal pressure of the pressurization mechanism forces the stem to return to its relaxed state.

A hydration delivery attachment 13 can be secured with respect to the pressurized reservoir 12 so that the delivery attachment 13 is accessible outside of the receiver 11. The hydration delivery attachment 13 can be constructed of a rigid and durable material, for example plastic or metal. For example, the hydration delivery attachment 13 can be secured to the stem of the described aerosol mechanism. The delivery attachment 13 has a connecting end 14 that receives liquid from the pressurized reservoir 12. Opposite the connecting end 14, the delivery attachment 13 has a delivery end 16 with an opening 18 sufficient that delivers the pressurized liquid to a user upon actuation of the pressurization mechanism. The delivery end 16 is larger than the connecting end 14, for example the delivery attachment 13 can be tapered larger from the connecting end to the delivery end, as shown throughout the various drawing figures. The pressurized reservoir 12 and hydration delivery attachment 13 can be pre-pressurized and disposable for one time use, or the reservoir 12 can be of a rechargeable refillable reusable nature.

Upon application of a downward force to the pressurization mechanism through the hydration delivery attachment 13, the pressurized liquid is expressed or projected under pressure in a fine mist to allow for delivery of moisture to the oral cavity as well as the respiratory airways. The larger delivery end 16 of the delivery attachment 13 can function as a mouthpiece with a surface area sufficient to form a seal between user (e.g., the lips) and the delivery attachment 13 when downward pressure is applied to the pressurization mechanism via the delivery attachment 13, contents are released under pressure thereby creating a small amount of backpressure, which serves to slightly puff out or inflate user's cheeks, allowing moisture to be dispersed and delivered evenly and thoroughly to all areas of the oral cavity.

Optionally the hydration delivery attachment 13 can have a stop check to prevent unintended discharge. Optionally the delivery attachment 13 can have a cap for surface contact areas, such as the delivery end, where lips meet for hygiene purposes. Optionally the delivery attachment 13 can also have a shape and design that enables nasal delivery.

Figure 2:
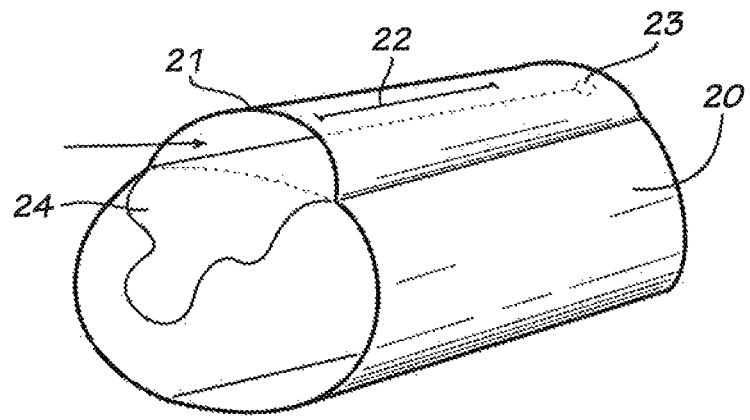
FIG. 2 is a perspective view of a wearable oral hydration apparatus with a shorter wearable housing base according to a second example embodiment.

FIG. 2 shows a second embodiment with a shorter wearable housing base 20 and a receiver 21 as well as examples of possible access to load a reservoir into the receiver. A drop down flap 24 can cover the receiver opening at one end and secures with any suitable fastener system described above. Alternatively, a slot 22 that can be opened and closed with a similar fastener system can receive the reservoir. An opening 23 in the receiver 21 provides access to the reservoir.

Figure 3:
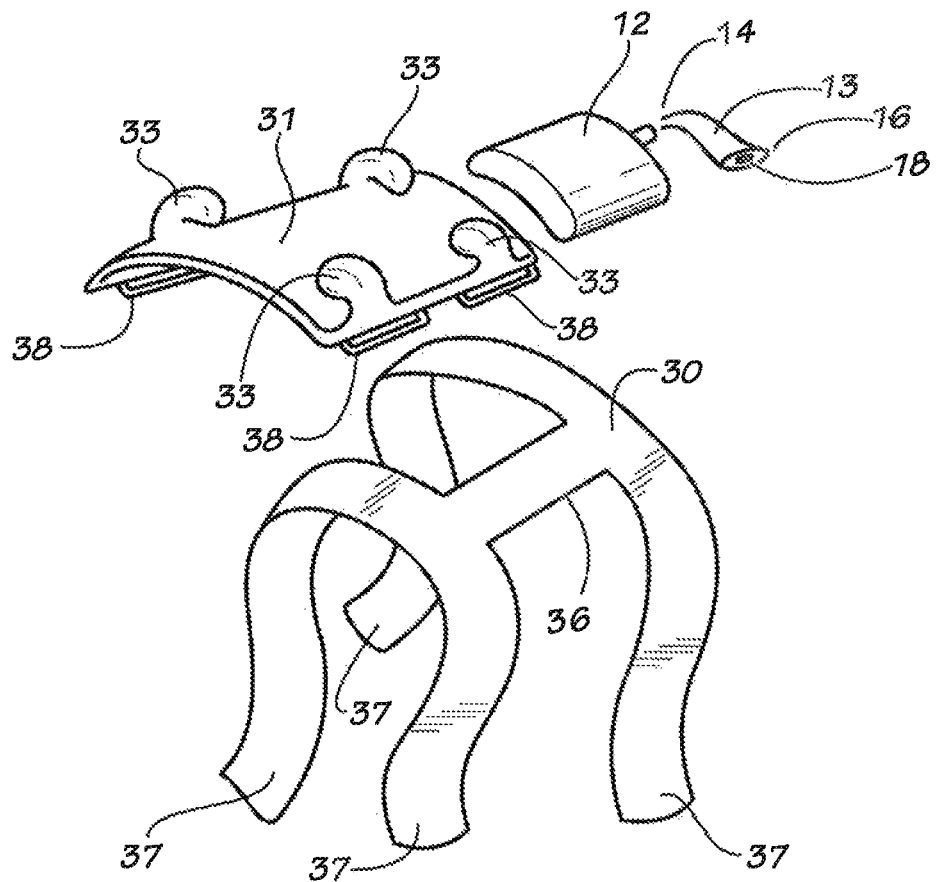
FIG. 3 is an exploded view of a wearable oral hydration apparatus utilizing injection molded plastics according to a third example embodiment.

FIG. 3 shows a third embodiment in which the housing base 30 is a plurality of flexible straps. The straps have one spine section 36 and four legs 37 extending from opposing sides of the spine. Each opposing pair of legs 37 can be wrapped around an appendage and secured to the other with fastening mechanisms, such as those described above. The receiver 31 is a flat rigid body having a shape that matches the outer surface of the reservoir 12. The receiver can be constructed of a rigid and durable material, for example molded plastic or metal. The receiver 31 has several grips 33 shown to be located at each corner of the receiver, however, the grips could be located along opposing sides. The grips 33 are spaced apart and located such that the reservoir 12 can be removed and inserted and secured within the grips. The grips 33 can be rigid static structures unitarily molded with the entire receiver 31. Alternatively, the grips 33 can be dynamic and movable to pinch or grab the reservoir 12. As shown, the receiver 31 can secure to the base 30 through several buckles 38 secured on the underside of the receiver. As shown, the buckles 38 are secured with proximity and opposite from the grips 33. In use, each strap arm 37 will insert through a buckle 38 so that the receiver 31 sits on top of the spine 36. The receiver 31 is then secured to an appendage by securing the arms 37 to each other around the appendage.

Figure 4:
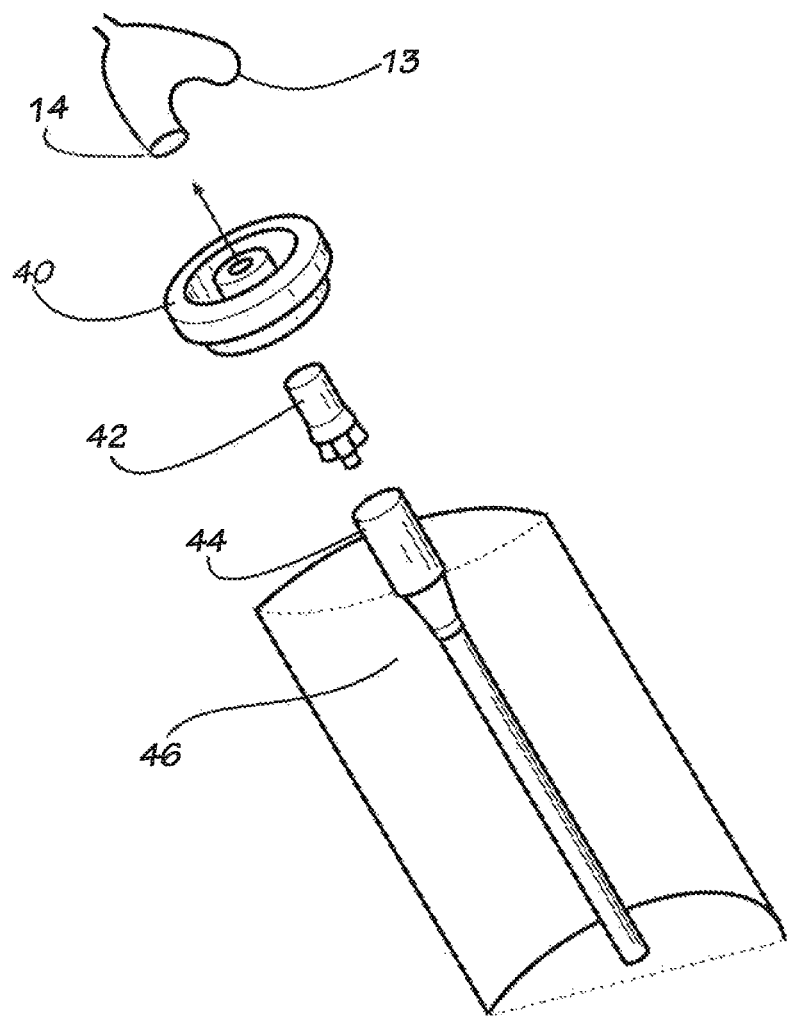
FIG. 4 is an exploded view of the wearable oral hydration apparatus of FIG. 1 showing how communication of the reservoir and orifice delivery attachment can be accomplished using commercial/current aerosol technology.

FIG. 4 shows an example pressurization mechanism (also referred to as a pressurize-release spray-dispensing mechanism) as described for use in FIG. 1. As shown, the pressurization mechanism can incorporate commercial/current sealed canister aerosol technology. The pressurized reservoir 12 includes a seal cup 40 to create a seal on the reservoir volume. A valve stem 42 protrudes through the seal cup 40. The valve stem 42 is secured within or communicates with a valve housing 44 and the valve cup 40 to cooperatively define a pressurize-release valve. The valve stem 42 secures to the oral delivery attachment 13 and downward pressure on the orifice delivery attachment causes a corresponding downward force on the stem to open the valve. Commercially available aerosol systems can include a stem gasket, and inner spring workings within the housing 44 that bias the valve stem 42 to the upper/outward (closed/containment) position. The housing 44 also connects a dip tube 46 to the stem 42. The dip tube 46 can utilize available aerosol canister technology to propel liquid in mist form out through standard stem 42 to the oral delivery attachment 13.

It is to be understood that this invention is not limited to the specific devices, methods, conditions, or parameters of the example embodiments described and/or shown herein, and that the terminology used herein is for the purpose of describing particular embodiments by way of example only. Thus, the terminology is intended to be broadly construed and is not intended to be unnecessarily limiting of the claimed invention. For example, as used in the specification including the appended claims, the singular forms "a," "an," and "the" include the plural, the term "or" means "and/or," and reference to a particular numerical value includes at least that particular value, unless the context clearly dictates otherwise. In addition, any methods described herein are not intended to be limited to the sequence of steps described but can be carried out in other sequences, unless expressly stated otherwise herein.

While the claimed invention has been shown and described in example forms, it will be apparent to those skilled in the art that many modifications, additions, and deletions can be made therein without departing from the spirit and scope of the invention as defined by the following claims.

What is claimed is:

1. A portable system for hydrating an oral cavity of a user to relieve xerostomia, the hydrating system comprising:
   a pressurized reservoir including a rigid container and a pressure-release spray-dispensing mechanism, wherein the container holds a volume of a hydrating liquid under pressure, and wherein the pressure-release spray-dispensing mechanism includes a valve stem movably actuatable by the user to release the pressurized hydrating liquid from the container in the form of a mist;
   a base configured to removably mount to and be worn on an appendage of the user for portability of the hydrating system, wherein the base includes a receiver adapted to removably support the pressurized reservoir on the base; and
   a hydration delivery attachment that is coupled to the pressurized reservoir and configured to receive and deliver the hydrating-liquid mist upon actuation of the valve stem, wherein the delivery attachment includes a connecting end and a delivery end with an opening, wherein the hydrating system is positionable with the delivery end opening delivering the hydrating-liquid mist into the oral cavity of the user to relieve the xerostomia.

2. The hydrating system of claim 1, wherein the valve stem is an aerosol valve.

3. The hydrating system of claim 1, wherein the appendage is a forearm, wrist, or both, and wherein the base includes a tube that is configured to releasably secure to the forearm, wrist, or both.

4. The hydrating system of claim 1, wherein the reservoir receiver includes a pocket that is configured to receive the pressurized reservoir.

5. The hydrating system of claim 1, wherein the base includes a curved plate and the reservoir receiver includes at least two grips extending from the curved plate and configured to releasably secure the pressurized reservoir.

6. The hydrating system of claim 5, further comprising a plurality of straps releasably securing the curved plate to the appendage.

7. The hydrating system of claim 6, wherein the plurality of straps are configured to releasably wrap around an appendage.

8. A method for delivering mist hydration to the oral cavity, the method comprising:
   providing the hydrating device of claim 1;
   securing the pressurized reservoir to the appendage using the base; and
   applying an actuating force to the valve stem to release the hydrating liquid from the reservoir, as the mist and deliver the hydrating-liquid mist through the delivery attachment and into the oral cavity.

9. The hydrating system of claim 1, wherein the hydrating liquid includes water.

10. The hydrating system of claim 1, wherein the delivery attachment is rigid and the connecting end of the delivery attachment is coupled to the valve stem of the pressurized reservoir so that the valve stem is depressed upon depressing of the rigid delivery attachment to dispense the hydrating-liquid mist.

11. The hydrating system of claim 1, wherein the delivery end of the delivery attachment is larger than the connecting end of the delivery attachment.

12. The hydrating system of claim 11, wherein the delivery attachment is tapered larger from the connecting end to the delivery end.

13. The hydrating system of claim 1, wherein the delivery attachment is configured so that the user can apply a pressing force to the delivery end of the delivery attachment to form a seal between the user and the delivery end, wherein when the pressure-release spray-dispensing mechanism is actuated, the hydrating-liquid mist released and delivered into the oral cavity remains pressurized and therefore distends the oral cavity to provide generally even and thorough dispersal of the hydrating-liquid mist within the oral cavity.

14. The hydrating system of claim 13, wherein the delivery end of the delivery attachment forms a mouthpiece that can be pressed against lips of the user to form the seal between the user and the delivery end.

15. A portable system for hydrating an oral cavity of a user to relieve xerostomia, the hydrating system comprising:
   a pressurized reservoir including a rigid container and a pressure-release spray-dispensing mechanism, wherein the container holds a volume of a liquid water under pressure, and wherein the pressure-release spray-dispensing mechanism includes a valve stem movably actuatable by the user to release the pressurized liquid water from the container in the form of a water mist;
   a base configured to removably mount to and be worn on an appendage of the user for portability of the hydrating system, wherein the base includes a receiver adapted to removably support the pressurized reservoir on the base; and a hydration delivery attachment that is coupled to the pressurized reservoir and configured to receive and deliver the water mist upon actuation of the valve stem, wherein the delivery attachment includes a connecting end and a delivery end with an opening, wherein the hydrating system is positionable with the delivery end opening delivering the water mist into the oral cavity of the user to relieve the xerostomia, wherein the delivery attachment is rigid and the connecting end of the delivery attachment is coupled to the valve stem of the pressurized reservoir so that the valve stem is depressed upon depressing of the rigid delivery attachment to dispense the water mist, wherein the delivery end of the delivery attachment is larger than the connecting end of the delivery attachment, the delivery attachment is tapered larger from the connecting end to the delivery end, and the delivery end forms a mouthpiece with a contacting surface area such that the user can press the delivery-end mouthpiece relative to and against lips of the user to form a seal between the user and the delivery-end mouthpiece, wherein when the pressure-release spray-dispensing mechanism is actuated, the water mist released and delivered into the oral cavity remains pressurized and therefore distends the oral cavity to provide generally even and thorough dispersal of the water mist within the oral cavity.

16. The hydrating system of claim 15, wherein the valve stem is an aerosol valve.

17. The hydrating system of claim 15, wherein the appendage is a forearm, wrist, or both, and wherein the base includes a tube that is configured to releasably secure to the forearm, wrist, or both.

18. The hydrating system of claim 17, wherein the reservoir receiver includes a pocket that is configured to receive the pressurized reservoir.

* * * * *